(12) United States Patent
Mignogna et al.

(10) Patent No.: US 9,714,303 B2
(45) Date of Patent: Jul. 25, 2017

(54) CATALYST COMPONENTS FOR THE POLYMERIZATION OF OLEFINS

(71) Applicant: Basell Polyolefine Italia S.r.l., Milan (IT)

(72) Inventors: Alessandro Mignogna, Ferrara (IT); Reynald Chevalier, Frankfurt (DE); Simona Guidotti, Ferrera (IT); Dario Liguori, Ferrara (IT); Giampiero Morini, Ferrara (IT); Martin Schneider, Hochheim (DE)

(73) Assignee: Basell Poliolefine Italia S.r.l., Milan (IT)

( * ) Notice: Subject to any disclaimer, the term of this patent is extended or adjusted under 35 U.S.C. 154(b) by 0 days.

(21) Appl. No.: 14/891,632

(22) PCT Filed: May 13, 2014

(86) PCT No.: PCT/EP2014/059717
§ 371 (c)(1),
(2) Date: Nov. 16, 2015

(87) PCT Pub. No.: WO2014/184171
PCT Pub. Date: Nov. 20, 2014

(65) Prior Publication Data
US 2016/0115261 A1    Apr. 28, 2016

(30) Foreign Application Priority Data
May 14, 2013   (EP) ..................................... 13167701

(51) Int. Cl.
*C08F 110/06*   (2006.01)
*C07C 271/44*   (2006.01)

(52) U.S. Cl.
CPC .......... *C08F 110/06* (2013.01); *C07C 271/44* (2013.01); *C07C 2101/14* (2013.01); *C07C 2102/08* (2013.01)

(58) Field of Classification Search
CPC ............................. C08F 110/06; C07C 271/44
See application file for complete search history.

(56) References Cited

U.S. PATENT DOCUMENTS

| | | | |
|---|---|---|---|
| 7,388,061 B2 | 6/2008 | Gao et al. | |
| 2005/0119427 A1 | 6/2005 | Wei et al. | |
| 2005/0239636 A1 | 10/2005 | Gao et al. | |
| 2011/0130529 A1 | 6/2011 | Coalter, III et al. | |

FOREIGN PATENT DOCUMENTS

| | | |
|---|---|---|
| CN | 1831017 A | 9/2006 |
| EP | 1666505 A1 | 6/2006 |
| JP | 2004091513 A | 3/2004 |

OTHER PUBLICATIONS

PCT International Search Report & Written Opinion mailed Jul. 1, 2014 for PCT/EP2014/059717.

*Primary Examiner* — Catherine S Branch

(57) ABSTRACT

A solid catalyst component for the polymerization of olefins comprising Mg, Ti, Cl and at least an electron donor compound which is the reaction product obtained by bringing into contact a Mg compound and a Ti compound having at least a Ti-halogen bond with an electron donor selected from specific diphenol derivatives.

14 Claims, No Drawings

CATALYST COMPONENTS FOR THE POLYMERIZATION OF OLEFINS

This application is the U.S. National Phase of PCT International Application PCT/EP2014/059717, filed May 13, 2014, claiming benefit of priority to European Patent Application No. 13167701.5, filed May 14, 2013, the contents of which are incorporated herein by reference in its entirety.

FIELD OF THE INVENTION

The present technology relates to catalyst components for the polymerization of olefins, in particular propylene, comprising a Mg dihalide based support on which are supported Ti atoms and an electron donor selected from a specific class of diphenol derivatives. The present technology further relates to the catalysts obtained from said components and to their use in processes for the polymerization of olefins in particular propylene.

BACKGROUND OF THE INVENTION

Catalyst components for the stereospecific polymerization of olefins are widely known in the art. Concerning the polymerization of propylene, the most spread out catalyst family belongs to the Ziegler-Natta category and in general terms it comprises a solid catalyst component, constituted by a magnesium dihalide on which are supported a titanium compound and an internal electron donor compound, used in combination with an Al-alkyl compound. Conventionally however, when a higher crystallinity of the polymer is required, also an external donor (for example an alkoxysilane) is needed in order to obtain higher isotacticity. One of the preferred classes of internal donors is constituted by the esters of phthalic acid, diisobutylphthalate being the most used. The phthalates are used as internal donors in combination with alkylalkoxysilanes as external donor. This catalyst system gives good performances in terms of activity, isotacticity and xylene insolubility. One of the problems associated with the use of this catalyst system is that the phthalates have recently raised concerns due to the medical issues associated with their use and some compounds within this class have been classified as source of heavy health problems. Consequently, research activities have been devoted to discover alternative classes of internal donors for use in the preparation of catalyst components for propylene polymerization. U.S. Pat. No. 7,388,061 discloses diesters belonging to the formula $R^1$—CO—O—$CR^3R^4$-A-$CR^5R^6$—O—CO—$R^2$ in which $R^1$ and $R^2$ groups, which may be identical or different, can be substituted or unsubstituted hydrocarbyl having 1 to 20 carbon atoms, $R^3$—$R^6$ groups, which may be identical or different, can be selected from the group consisting of hydrogen, halogen or substituted or unsubstituted hydrocarbyl having 1 to 20 carbon atoms, $R^1$—$R^6$ groups optionally contain one or more hetero-atoms replacing carbon, hydrogen atom or the both, said hetero-atom is selected from the group consisting of nitrogen, oxygen, sulfur, silicon, phosphorus and halogen atom, two or more of $R^3$—$R^6$ groups can be linked to form saturated or unsaturated monocyclic or polycyclic ring; A is a single bond or bivalent linking group with chain length between two free radicals being 1-10 atoms, wherein said bivalent linking group is selected from the group consisting of aliphatic, alicyclic and aromatic bivalent radicals, and can carry $C_1$-$C_{20}$ linear or branched substituents; one or more of carbon atoms and/or hydrogen atoms on above-mentioned bivalent linking group and substituents can be replaced by a hetero-atom selected from the group consisting of nitrogen, oxygen, sulfur, silicon, phosphorus, and halogen atom, and two or more said substituents on the linking group as well as above-mentioned $R^3$—$R^6$ groups can be linked to form saturated or unsaturated monocyclic or polycyclic ring. The very broad definition of the A group encompasses a huge number of diol skeletons from which corresponding diesters can be generated. However, when the bridging group A includes an aromatic structure (like phenyl or diphenyl as in examples 4, 17, 62, 79-80) the balance activity/stereospecificity is greatly unsatisfactory and in fact the same ester groups perform much better when associated to diols skeleton based on aliphatic structure.

SUMMARY OF THE INVENTION

Surprisingly, the applicant has found that a particular class of donors which results from the combination of a possibly substituted diphenol based structure with functional groups of a different nature capable to react with the hydroxy group of the diphenol, is able to generate catalysts having improved balance of activity and stereospecificity over previously disclosed aromatic diolesters.

It is herein disclosed a solid catalyst component for the polymerization of olefins comprising Mg, Ti, Cl and at least an electron donor compound which is the reaction product obtained by bringing into contact a Mg compound and a Ti compound having at least a Ti-halogen bond with a diphenol derivative of formula (I)

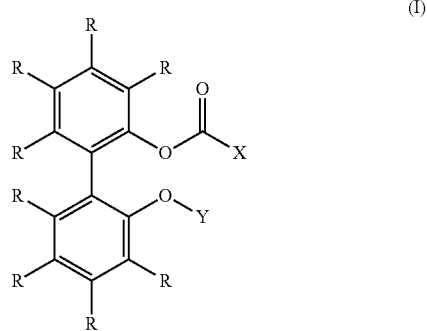

(I)

in which X is selected from $R^1$, —$OR^1$ and —$NR_2$, Y is selected from hydrogen, $R^1$, —$COR^1$, —$CONR_2$, and -$MZ_{(n-1)}$ the R groups, equal to or different from each other, are selected from hydrogen, halogen and $C_1$-$C_{15}$ hydrocarbon groups, optionally containing an heteroatom selected from halogen, P, S, N, O and Si, which can be fused together to form one or more cycles, M is an element belonging to group 2, 4-13 of the Periodic Table of Elements, n is the valence of M, Z is halogen or $OR^1$ and the $R^1$ group is a $C_1$-$C_{15}$ aliphatic or aromatic hydrocarbon group, with the proviso that when X is a substituted or unsubstituted phenyl group, and Y is a substituted or unsubstituted benzoyl group at least one of the R groups on the phenyl rings of the structure of formula (I) is not hydrogen.

DETAILED DESCRIPTION OF THE INVENTION

The diphenol of formula (I) may comprise at least one R group on the phenyl ring that is different from hydrogen and selected from halogen or $C_1$-$C_{15}$ hydrocarbon groups, including at least two of the R groups, at least 3 and at least 4 of the R groups are different from hydrogen. In a particular embodiment, six of the R groups are different from hydrogen. In some embodiments, the two phenyl rings of the diphenol structure of formula (I) have the same substitution pattern. Accordingly, when the R groups different from hydrogen are in an even number (2, 4, 6, etc.) the R groups are distributed equally in number and position on the two phenyl rings. The R groups different from hydrogen may be selected from $C_1$-$C_{15}$ hydrocarbon groups and particularly from $C_1$-$C_{10}$ alkyl groups. The R groups different from hydrogen may be $C_1$-$C_5$ alkyl groups that are linear or branched, including methyl and t-butyl groups.

$R^1$ groups may be selected from $C_1$-$C_{10}$ alkyl groups and $C_6$-$C_{15}$ aryl or alkylaryl groups. Among alkyl groups, linear $C_1$-$C_5$ alkyl groups such as methyl, ethyl and propyl may be used. Aryl or alkylaryl groups may be phenyl groups substituted with halogen and/or $C_1$-$C_5$ alkyl groups.

R radicals in the —$NR_2$ and —$CONR_2$ groups may be selected from $C_1$-$C_{10}$ alkyl groups, including linear $C_1$-$C_5$ alkyl groups such as methyl, ethyl and propyl.

M may be selected from Mg, Ti, and Al.

Z may be chlorine or $OR^1$, in which $R^1$ groups are selected from $C_1$-$C_{10}$ alkyl groups.

Possible combinations between X and Y groups are those in which X is $R^1$ and Y is selected from hydrogen, $R^1$, —$COR^1$, and —$CONR_2$, including where X is a $C_6$-$C_{15}$ aryl or alkylaryl group such as methyl.

In addition, structures in which X is —$NR_2$ and Y is selected from hydrogen and —$COR^1$ in which $R^1$ has the meaning explained above may be used. In this case $R^1$ may be a $C_6$-$C_{15}$ aryl or alkylaryl group and R is a linear $C_1$-$C_5$ alkyl group. Non limiting examples of structures of formula (I) are the following: 2'-hydroxy-[1,1'-biphenyl]-2-yl 4-propylbenzoate, 2'-hydroxy-[1,1'-biphenyl]-2-yl acetate, 2'-hydroxy-[1,1'-biphenyl]-2-yl benzoate, 2'-hydroxy-[1,1'-biphenyl]-2-yl pentanoate, 2'-hydroxy-[1,1'-biphenyl]-2-yl pivalate, 2'-methoxy-[1,1'-biphenyl]-2-yl 4-propylbenzoate, 2'-methoxy-[1,1'-biphenyl]-2-yl acetate, 2'-methoxy-[1,1'-biphenyl]-2-yl benzoate, 2'-methoxy-[1,1'-biphenyl]-2-yl pentanoate, 2'-methoxy-[1,1'-biphenyl]-2-yl pivalate, 2'-hydroxy-[1,1'-biphenyl]-2-yl diethylcarbamate, 2'-methoxy-[1,1'-biphenyl]-2-yl diethylcarbamate, ethyl(2'-hydroxy-[1,1'-biphenyl]-2-yl) carbonate, ethyl(2'-methoxy-[1,1'-biphenyl]-2-yl) carbonate, magnesium 2'-(benzoyloxy)-[1,1'-biphenyl]-2-olate chloride, magnesium 2'-((diethylcarbamoyl)oxy)-[1,1'-biphenyl]-2-olate chloride, magnesium 2'-acetoxy-[1,1'-biphenyl]-2-olate chloride, magnesium 2'-((ethoxycarbonyl)oxy)-[1,1'-biphenyl]-2-olate chloride, magnesium 2'-((4-propylbenzoyl)oxy)-[1,1'-biphenyl]-2-olate chloride, magnesium 2'-(pivaloyloxy)-[1,1'-biphenyl]-2-olate chloride, magnesium 2'-(pentanoyloxy)-[1,1'-biphenyl]-2-olate chloride, ((2'-(benzoyloxy)-[1,1'-biphenyl]-2-yl)oxy)titanium(IV) chloride, ((2'-((diethylcarbamoyl)oxy)-[1,1'-biphenyl]-2-yl)oxy)titanium(IV) chloride, ((2'-acetoxy-[1,1'-biphenyl]-2-yl)oxy)titanium(IV) chloride, ((2'-((4-propylbenzoyl)oxy)-[1,1'-biphenyl]-2-yl)oxy)titanium(IV) chloride, ((2'-((ethoxycarbonyl)oxy)-[1,1'-biphenyl]-2-yl)oxy)titanium(IV) chloride, ((2'-(pivaloyloxy)-[1,1'-biphenyl]-2-yl)oxy)titanium(IV) chloride, ((2'-(pentanoyloxy)-[1,1'-biphenyl]-2-yl)oxy)titanium(IV) chloride, 2'-((diethylcarbamoyl)oxy)-[1,1'-biphenyl]-2-yl acetate, 2'-((diethylcarbamoyl)oxy)-[1,1'-biphenyl]-2-yl pentanoate, 2'-((diethylcarbamoyl)oxy)-[1,1'-biphenyl]-2-yl pivalate, 2'-((ethoxycarbonyl)oxy)-[1,1'-biphenyl]-2-yl acetate, 2'-((ethoxycarbonyl)oxy)-[1,1'-biphenyl]-2-yl pentanoate, 2'-((ethoxycarbonyl)oxy)-[1,1'-biphenyl]-2-yl pivalate, 2'-(pivaloyloxy)-[1,1'-biphenyl]-2-yl pentanoate, 2'-acetoxy-[1,1'-biphenyl]-2-yl pentanoate, 2'-acetoxy-[1,1'-biphenyl]-2-yl pivalate, [1,1'-biphenyl]-2,2'-diyl bis(2,2-dimethylpropanoate), [1,1'-biphenyl]-2,2'-diyl diacetate, [1,1'-biphenyl]-2,2'-diyl dipentanoate, 2'-((ethoxycarbonyl)oxy)-[1,1'-biphenyl]-2-yl diethylcarbamate, [1,1'-biphenyl]-2,2'-diyl bis(diethylcarbamate), 5,5',6,6'-tetramethyl-[1,1'-biphenyl]-2,2'-diyl bis(2-methylbenzoate), 5,5',6,6'-tetramethyl-[1,1'-biphenyl]-2,2'-diyl bis(3,5-dimethylbenzoate), 6'-((cyclohexanecarbonyl)oxy)-2',3',5,6-tetramethyl-[1,1'-biphenyl]-2-yl benzoate, 5,5',6,6'-tetramethyl-[1,1'-biphenyl]-2,2'-diyl bis(4-propylbenzoate), 2',3',5,6-tetramethyl-6'-(pentanoyloxy)-[1,1'-biphenyl]-2-yl benzoate, 2',3',5,6-tetramethyl-6'-(pivaloyloxy)-[1,1'-biphenyl]-2-yl benzoate, 2',3',5,6-tetramethyl-6'-(pivaloyloxy)-[1,1'-biphenyl]-2-yl pentanoate, 5,5',6,6'-tetramethyl-[1,1'-biphenyl]-2,2'-diyl bis(2,2-dimethylpropanoate), 5,5',6,6'-tetramethyl-[1,1'-biphenyl]-2,2'-diyl diacetate, 5,5',6,6'-tetramethyl-[1,1'-biphenyl]-2,2'-diyl dibenzoate, 5,5',6,6'-tetramethyl-[1,1'-biphenyl]-2,2'-diyl dipentanoate, 6'-((diethylcarbamoyl)oxy)-2',3',5,6-tetramethyl-[1,1'-biphenyl]-2-yl acetate, 6'-((diethylcarbamoyl)oxy)-2',3',5,6-tetramethyl-[1,1'-biphenyl]-2-yl benzoate, 6'-((diethylcarbamoyl)oxy)-2',3',5,6-tetramethyl-[1,1'-biphenyl]-2-yl pentanoate, 6'-((diethylcarbamoyl)oxy)-2',3',5,6-tetramethyl-[1,1'-biphenyl]-2-yl pivalate, 6'-((ethoxycarbonyl)oxy)-2',3',5,6-tetramethyl-[1,1'-biphenyl]-2-yl acetate, 6'-((ethoxycarbonyl)oxy)-2',3',5,6-tetramethyl-[1,1'-biphenyl]-2-yl benzoate, 6'-((ethoxycarbonyl)oxy)-2',3',5,6-tetramethyl-[1,1'-biphenyl]-2-yl pentanoate, 6'-((ethoxycarbonyl)oxy)-2',3',5,6-tetramethyl-[1,1'-biphenyl]-2-yl pivalate, 6'-acetoxy-2',3',5,6-tetramethyl-[1,1'-biphenyl]-2-yl benzoate, 6'-acetoxy-2',3',5,6-tetramethyl-[1,1'-biphenyl]-2-yl pentanoate, 6'-acetoxy-2',3',5,6-tetramethyl-[1,1'-biphenyl]-2-yl pivalate, 5,5',6,6'-tetramethyl-[1,1'-biphenyl]-2,2'-diyl bis(diethylcarbamate), 6'-((ethoxycarbonyl)oxy)-2',3',5,6-tetramethyl-[1,1'-biphenyl]-2-yl diethylcarbamate, 6'-hydroxy-2',3',5,6-tetramethyl-[1,1'-biphenyl]-2-yl acetate, 6'-hydroxy-2',3',5,6-tetramethyl-[1,1'-biphenyl]-2-yl benzoate, 6'-hydroxy-2',3',5,6-tetramethyl-[1,1'-biphenyl]-2-yl pentanoate, 6'-hydroxy-2',3',5,6-tetramethyl-[1,1'-biphenyl]-2-yl pivalate, 6'-methoxy-2',3',5,6-tetramethyl-[1,1'-biphenyl]-2-yl acetate, 6'-methoxy-2',3',5,6-tetramethyl-[1,1'-biphenyl]-2-yl benzoate, 6'-methoxy-2',3',5,6-tetramethyl-[1,1'-biphenyl]-2-yl pentanoate, 6'-methoxy-2',3',5,6-tetramethyl-[1,1'-biphenyl]-2-yl pivalate, 6'-hydroxy-2',3',5,6-tetramethyl-[1,1'-biphenyl]-2-yl diethylcarbamate, 6'-methoxy-2',3',5,6-tetramethyl-[1,1'-biphenyl]-2-yl diethylcarbamate, ((2',3',5,6-tetramethyl-6'-(pivaloyloxy)-[1,1'-biphenyl]-2-yl)oxy)titanium(IV) chloride, ((6'-((diethylcarbamoyl)oxy)-2',3',5,6-tetramethyl-[1,1'-biphenyl]-2-yl)oxy)titanium(IV) chloride, ((6'-acetoxy-2',3',5,6-tetramethyl-[1,1'-biphenyl]-2-yl)oxy)titanium(IV) chloride, ((2',3',5,6-tetramethyl-6'-(pentanoyloxy)-[1,1'-biphenyl]-2-yl)oxy)titanium(IV) chloride, ((6'-(benzoyloxy)-2',3',5,6-tetramethyl-[1,1'-biphenyl]-2-yl)oxy)titanium(IV) chloride, magnesium 2',3',5,6-tetramethyl-6'-(pivaloyloxy)-[1,1'-biphenyl]-2-olate chloride, magnesium 6'-((diethylcarbamoyl)oxy)-2',3',5,6-tetramethyl-[1,1'-biphenyl]-2-olate chloride, magnesium 6'-acetoxy-2',3',5,6-tetramethyl-[1,1'-biphenyl]-2-olate chloride, magnesium 2',3',5,6-tetramethyl-6'-(pentanoyloxy)-[1,1'-biphenyl]-2-olate chloride, magnesium 6'-(benzoyloxy)-2',3',5,6-tetramethyl-[1,1'-biphenyl]-2-olate chloride, 2'-acetoxy-3,3'-di-tert-butyl-5,5',6,6'-tetramethyl-[1,1'-biphenyl]-2-yl benzoate, 2'-acetoxy-3,3'-di-tert-butyl-5,5',6, 6'-tetramethyl-[1,1'-biphenyl]-2-yl pentanoate, 2'-acetoxy-3,3'-di-tert-butyl-5,5',6,6'-tetramethyl-[1,1'-biphenyl]-2-yl pivalate, 3,3'-di-tert-butyl-2'-((diethylcarbamoyl)oxy)-5,5',6,6'-tetramethyl-[1,1'-biphenyl]-2-yl acetate, 3,3'-di-tert-butyl-2'-((diethylcarbamoyl)oxy)-5,5',6,6'-tetramethyl-[1,1'-biphenyl]-2-yl benzoate, 3,3'-di-tert-butyl-2'-((diethylcarbamoyl)oxy)-5,5',6,6'-tetramethyl-[1,1'-biphenyl]-2-yl pentanoate, 3,3'-di-tert-butyl-2'-((diethylcarbamoyl)oxy)-5,5',6,6'-tetramethyl-[1,1'-biphenyl]-2-yl pivalate, 3,3'-di-tert-butyl-2'-((ethoxycarbonyl)oxy)-5,5',6,6'-tetramethyl-[1,1'-biphenyl]-2-yl acetate, 3,3'-di-tert-butyl-2'-((ethoxycarbonyl)oxy)-5,5',6,6'-tetramethyl-[1,1'-biphenyl]-2-yl benzoate, 3,3'-di-tert-butyl-2'-((ethoxycarbonyl)oxy)-5,5',6,6'-tetramethyl-[1,1'-biphenyl]-2-yl pentanoate, 3,3'-di-tert-butyl-2'-((ethoxycarbonyl)oxy)-5,5',6,6'-tetramethyl-[1,1'-biphenyl]-2-yl pivalate, 3,3'-di-tert-butyl-5,5',6,6'-tetramethyl-2'-(pentanoyloxy)-[1,1'-biphenyl]-2-yl benzoate, 3,3'-di-tert-butyl-5,5',6,6'-tetramethyl-2'-(pivaloyloxy)-[1,1'-biphenyl]-2-yl benzoate, 3,3'-di-tert-butyl-5,5',6,6'-tetramethyl-2'-(pivaloyloxy)-[1,1'-biphenyl]-2-yl pentanoate, 3,3'-di-tert-butyl-5,5',6,6'-tetramethyl-[1,1'-biphenyl]-2,2'-diyl bis(2,2-dimethylpropanoate), 3,3'-di-tert-butyl-5,5',6,6'-tetramethyl-[1,1'-biphenyl]-2,2'-diyl diacetate, 3,3'-di-tert-butyl-5,5',6,6'-tetramethyl-[1,1'-biphenyl]-2,2'-diyl dibenzoate, 3,3'-di-tert-butyl-5,5',6,6'-tetramethyl-[1,1'-biphenyl]-2,2'-diyl dipentanoate, 3,3'-di-tert-butyl-2'-((ethoxycarbonyl)oxy)-5,5',6,6'-tetramethyl-[1,1'-biphenyl]-2-yl diethylcarbamate, 3,3'-di-tert-butyl-5,5',6,6'-tetramethyl-[1,1'-biphenyl]-2,2'-diyl bis(diethylcarbamate), 3,3'-di-tert-butyl-5,5',6,6'-tetramethyl-[1,1'-biphenyl]-2,2'-diyl bis(4-propylbenzoate), 3,3'-di-tert-butyl-2'-hydroxy-5,5',6,6'-tetramethyl-[1,1'-biphenyl]-2-yl acetate, 3,3'-di-tert-butyl-2'-hydroxy-5,5',6,6'-tetramethyl-[1,1'-biphenyl]-2-yl benzoate, 3,3'-di-tert-butyl-2'-hydroxy-5,5',6,6'-tetramethyl-[1,1'-biphenyl]-2-yl pentanoate, 3,3'-di-tert-butyl-2'-hydroxy-5,5',6,6'-tetramethyl-[1,1'-biphenyl]-2-yl pivalate, 3,3'-di-tert-butyl-2'-methoxy-5,5',6,6'-tetramethyl-[1,1'-biphenyl]-2-yl acetate, 3,3'-di-tert-butyl-2'-methoxy-5,5',6,6'-tetramethyl-[1,1'-biphenyl]-2-yl benzoate, 3,3'-di-tert-butyl-2'-methoxy-5,5',6,6'-tetramethyl-[1,1'-biphenyl]-2-yl pentanoate, 3,3'-di-tert-butyl-2'-methoxy-5,5',6,6'-tetramethyl-[1,1'-biphenyl]-2-yl pivalate, 3,3'-di-tert-butyl-2'-hydroxy-5,5',6,6'-tetramethyl-[1,1'-biphenyl]-2-yl diethylcarbamate, 3,3'-di-tert-butyl-2'-methoxy-5,5',6,6'-tetramethyl-[1,1'-biphenyl]-2-yl diethylcarbamate, ((3,3'-di-tert-butyl-5,5',6,6'-tetramethyl-2'-(pivaloyloxy)-[1,1'-biphenyl]-2-yl)oxy)titanium(IV) chloride, ((3,3'-di-tert-butyl-5,5',6,6'-tetramethyl-2'-(pentanoyloxy)-[1,1'-biphenyl]-2-yl)oxy)titanium(IV) chloride, ((2'-acetoxy-3,3'-di-tert-butyl-5,5',6,6'-tetramethyl-[1,1'-biphenyl]-2-yl)oxy)titanium(IV) chloride, ((3,3'-di-tert-butyl-2'-((diethylcarbamoyl)oxy)-5,5',6,6'-tetramethyl-[1,1'-biphenyl]-2-yl)oxy)titanium(IV) chloride, magnesium 2'-acetoxy-3,3'-di-tert-butyl-5,5',6,6'-tetramethyl-[1,1'-biphenyl]-2-olate chloride, ((2'-(benzoyloxy)-3,3'-di-tert-butyl-5,5',6,6'-tetramethyl-[1,1'-biphenyl]-2-yl)oxy)titanium(IV) chloride, magnesium 3,3'-di-tert-butyl-2'-((diethylcarbamoyl)oxy)-5,5',6,6'-tetramethyl-[1,1'-biphenyl]-2-olate chloride, magnesium 3,3'-di-tert-butyl-5,5',6,6'-tetramethyl-2'-(pentanoyloxy)-[1,1'-biphenyl]-2-olate chloride, magnesium 3,3'-di-tert-butyl-5,5',6,6'-tetramethyl-2'-(pivaloyloxy)-[1,1'-biphenyl]-2-olate chloride, magnesium 2'-(benzoyloxy)-3,3'-di-tert-butyl-5,5',6,6'-tetramethyl-[1,1'-biphenyl]-2-olate chloride, 2'-((diethylcarbamoyl)oxy)-6,6'-dimethyl-[1,1'-biphenyl]-2-yl benzoate, 2'-hydroxy-6,6'-dimethyl-[1,1'-biphenyl]-2-yl benzoate, 6,6'-dimethyl-[1,1'-biphenyl]-2,2'-diyl dibenzoate, 2'-hydroxy-6,6'-dimethyl-[1,1'-biphenyl]-2-yl diethylcarbamate, 6,6'-dimethyl-[1,1'-biphenyl]-2,2'-diyl bis(diethylcarbamate), ((2'-(benzoyloxy)-6,6'-dimethyl-[1,1'-biphenyl]-2-yl)oxy)titanium(IV) chloride, ((2'-((diethylcarbamoyl)oxy)-6,6'-dimethyl-[1,1'-biphenyl]-2-yl)oxy)titanium(IV) chloride, magnesium 2'-(benzoyloxy)-6,6'-dimethyl-[1,1'-biphenyl]-2-olate chloride, magnesium 2'-((diethylcarbamoyl)oxy)-6,6'-dimethyl-[1,1'-biphenyl]-2-olate chloride, 2'-((diethylcarbamoyl)oxy)-[1,1'-binaphthalen]-2-yl acetate, 2'-((diethylcarbamoyl)oxy)-[1,1'-binaphthalen]-2-yl benzoate, 2'-((diethylcarbamoyl)oxy)-[1,1'-binaphthalen]-2-yl pentanoate, 2'-((diethylcarbamoyl)oxy)-[1,1'-binaphthalen]-2-yl pivalate, 2'-((ethoxycarbonyl)oxy)-[1,1'-binaphthalen]-2-yl acetate, 2'-((ethoxycarbonyl)oxy)-[1,1'-binaphthalen]-2-yl benzoate, 2'-((ethoxycarbonyl)oxy)-[1,1'-binaphthalen]-2-yl pentanoate, 2'-((ethoxycarbonyl)oxy)-[1,1'-binaphthalen]-2-yl pivalate, 2'-(pentanoyloxy)-[1,1'-binaphthalen]-2-yl benzoate, 2'-(pivaloyloxy)-[1,1'-binaphthalen]-2-yl benzoate, 2'-(pivaloyloxy)-[1,1'-binaphthalen]-2-yl pentanoate, 2'-acetoxy-[1,1'-binaphthalen]-2-yl benzoate, 2'-acetoxy-[1,1'-binaphthalen]-2-yl pentanoate, 2'-acetoxy-[1,1'-binaphthalen]-2-yl pivalate, [1,1'-binaphthalene]-2,2'-diyl bis (2,2-dimethylpropanoate), [1,1'-binaphthalene]-2,2'-diyl diacetate, [1,1'-binaphthalene]-2,2'-diyl dibenzoate, [1,1'-binaphthalene]-2,2'-diyl dipentanoate, 2'-((ethoxycarbonyl)oxy)-[1,1'-binaphthalen]-2-yl diethylcarbamate, [1,1'-binaphthalene]-2,2'-diyl bis(diethylcarbamate), 2'-hydroxy-[1,1'-binaphthalen]-2-yl, 2'-hydroxy-[1,1'-binaphthalen]-2-yl benzoate, 2'-hydroxy-[1,1'-binaphthalen]-2-yl pentanoate, 2'-hydroxy-[1,1'-binaphthalen]-2-yl pivalate, 2'-methoxy-[1,1'-binaphthalen]-2-yl acetate, 2'-methoxy-[1,1'-binaphthalen]-2-yl benzoate, 2'-methoxy-[1,1'-binaphthalen]-2-yl pentanoate, 2'-methoxy-[1,1'-binaphthalen]-2-yl pivalate, 2'-hydroxy-[1,1'-binaphthalen]-2-yl diethylcarbamate, 2'-methoxy-[1,1'-binaphthalen]-2-yl diethylcarbamate, magnesium 2'-(pivaloyloxy)-[1,1'-binaphthalen]-2-olate chloride, magnesium 2'-acetoxy-[1,1'-binaphthalen]-2-olate chloride, magnesium 2'-((diethylcarbamoyl)oxy)-[1,1'-binaphthalen]-2-olate chloride, magnesium 2'-(benzoyloxy)-[1,1'-binaphthalen]-2-olate chloride, magnesium 2'-(pentanoyloxy)-[1,1'-binaphthalen]-2-olate chloride, ((2'-((diethylcarbamoyl)oxy)-[1,1'-binaphthalen]-2-yl)oxy)titanium(IV) chloride, ((2'-acetoxy-[1,1'-binaphthalen]-2-yl)oxy)titanium(IV) chloride, ((2'-(pivaloyloxy)-[1,1'-binaphthalen]-2-yl)oxy)titanium(IV) chloride, ((2'-(pentanoyloxy)-[1,1'-binaphthalen]-2-yl)oxy)titanium(IV) chloride, ((2'-(benzoyloxy)-[1,1'-binaphthalen]-2-yl)oxy)titanium(IV) chloride, 2'-hydroxy-5,5',6,6',7,7',8,8'-octahydro-[1,1'-binaphthalen]-2-yl benzoate, 2,2',3,3'-tetrahydro-1H, 1'H-[4,4'-biindene]-5,5'-diyl dibenzoate, 5'-hydroxy-2,2',3,3'-tetrahydro-1H, 1'H-[4,4'-biinden]-5-yl benzoate, 5,5',6,6',7,7',8,8'-octahydro-[1,1'-binaphthalene]-2,2'-diyl dibenzoate, 6,6'-di-tert-butyl-2,2',3,3'-tetrahydro-1H, 1'H-[4,4'-biindene]-5,5'-diyl dibenzoate, 6,6'-di-tert-butyl-5'-hydroxy-2,2',3,3'-tetrahydro-1H,1'H-[4,4'-biinden]-5-yl benzoate.

The compounds falling in formula (I) can be added as such during the catalyst preparation process or, in the alternative, in the form of precursors that, due to reaction with other catalyst ingredients, are able to transform in the compounds of formula (I). In addition to the compounds of above formula (I) the solid catalyst components can also contain additional donors. Although there is no limitation on the type of additional donors, esters of benzoic acids possibly substituted with halogen or $C_1$-$C_{15}$ hydrocarbon groups on the phenyl ring may be used.

As explained above, the catalyst components as herein described can comprise, in addition to the above electron donors, Ti, Mg and halogen. In particular, the catalyst components comprise a titanium compound, having at least a Ti-halogen bond and the above mentioned electron donor compounds supported on a Mg halide. The magnesium halide may be $MgCl_2$. Patents U.S. Pat. Nos. 4,298,718 and 4,495,338 were the first to describe the use of these compounds in Ziegler-Natta catalysis. It is known from these patents that the magnesium dihalides in active form used as support or co-support in components of catalysts for the polymerization of olefins are characterized by X-ray spectra in which the most intense diffraction line that appears in the spectrum of the non-active halide is diminished in intensity and is replaced by a halo whose maximum intensity is displaced towards lower angles relative to that of the more intense line.

Titanium compounds that may be used in the preparation of the herein disclosed catalyst components are $TiCl_4$ and $TiCl_3$; furthermore, also Ti-haloalcoholates of formula $Ti(OR)_{m-y}X_y$ can be used, where m is the valence of titanium, y is a number between 1 and m−1, X is halogen and R is a hydrocarbon radical having from 1 to 10 carbon atoms.

The solid catalyst component described in the present application can contain Ti atoms in an amount higher than 2.5% wt, including higher than 3.0% with respect to the total weight of said catalyst component and an amount ranging from 2.5 to 8% of titanium.

The preparation of the solid catalyst component can be carried out according to several methods. One method comprises the reaction between magnesium alcoholates or chloroalcoholates (in particular chloroalcoholates prepared according to U.S. Pat. No. 4,220,554) and an excess of $TiCl_4$ in the presence of the electron donor compounds at a temperature of about 80 to 120° C.

The solid catalyst component can be prepared by reacting a titanium compound of formula $Ti(OR)_{m-y}X_y$, where m is the valence of titanium and y is a number between 1 and m, including $TiCl_4$, with a magnesium chloride deriving from an adduct of formula $MgCl_2 \cdot pROH$, where p is a number between 0.1 and 6, including from 2 to 3.5, and R is a hydrocarbon radical having 1-18 carbon atoms. The adduct can be suitably prepared in spherical form by mixing alcohol and magnesium chloride in the presence of an inert hydrocarbon immiscible with the adduct, operating under stirring conditions at the melting temperature of the adduct (100-130° C.). Then, the emulsion is quickly quenched, thereby causing the solidification of the adduct in form of spherical particles. Examples of spherical adducts prepared according to this procedure are described in U.S. Pat. Nos. 4,399,054 and 4,469,648. The obtained adduct can be directly reacted with Ti compound or it can be previously subjected to thermal controlled dealcoholation (80-130° C.) so as to obtain an adduct in which the number of moles of alcohol is lower than 3, including between 0.1 and 2.5. The reaction with the Ti compound can be carried out by suspending the adduct (dealcoholated or as such) in cold $TiCl_4$ (around 0° C.); the mixture is heated up to 80-130° C. and kept at this temperature for 0.5-2 hours. The treatment with $TiCl_4$ can be carried out one or more times. In some embodiments, the electron donor compound is added during the first treatment with $TiCl_4$ in an amount such as to have a Mg/donor ratio in the range of 2 to 15, including from 4 to 10. In case additional donors are present, the donor addition may be split. In particular, the additional donor may be added during the first treatment with $TiCl_4$ while the donor of formula (I) may be added during a second treatment with $TiCl_4$. The preparation of catalyst components in spherical form are described for example in European Patent Applications EP-A-395083, EP-A-553805, EP-A-553806, EPA601525 and WO98/44009.

The solid catalyst components obtained according to the above method show a surface area (by B.E.T. method) between 20 and 500 $m^2/g$, including between 50 and 400 $m^2/g$, and a total porosity (by B.E.T. method) higher than 0.2 $cm^3/g$, including between 0.2 and 0.6 $cm^3/g$. The porosity (Hg method) due to pores with radius up to 10.000 Å ranges from 0.3 to 1.5 $cm^3/g$, including from 0.45 to 1 $cm^3/g$.

The solid catalyst component has an average particle size ranging from 5 to 120 μm, including from 10 to 100 μm.

Regardless of the preparation method used, the final amount of the electron donor compound of formula (I) is such that its molar ratio with respect to the Ti atoms is from 0.01 to 2, including from 0.05 to 1.2.

The solid catalyst components can be converted into catalysts for the polymerization of olefins by reacting the components with organoaluminum compounds.

In particular, it is provided a catalyst for the polymerization of olefins $CH_2$=CHR, in which R is hydrogen or a hydrocarbyl radical with 1-12 carbon atoms, comprising the product obtained by contacting:
(i) the solid catalyst component as disclosed above and
(ii) an alkylaluminum compound and optionally,
(iii) an external electron donor compound The alkyl-Al compound (ii) may be chosen among the trialkyl aluminum compounds such as for example triethylaluminum, triisobutylaluminum, tri-n-butylaluminum, tri-n-hexylaluminum, and tri-n-octylaluminum. It is also possible to use alkylaluminum halides, alkylaluminum hydrides or alkylaluminum sesquichlorides, such as $AlEt_2Cl$ and $Al_2Et_3Cl_3$, possibly in mixture with the above cited trialkylaluminums.

External electron-donor compounds may include silicon compounds, ethers, esters, amines, heterocyclic compounds and particularly 2,2,6,6-tetramethylpiperidine and ketones.

Another class of external donor compounds is that of silicon compounds of formula $(R_7)_a(R_8)_bSi(OR_9)_c$, where a and b are integers from 0 to 2, c is an integer from 1 to 4 and the sum (a+b+c) is 4; $R_7$, $R_8$, and $R_9$, are radicals with 1-18 carbon atoms optionally containing heteroatoms. Silicon compounds in which a is 1, b is 1, c is 2, at least one of $R_7$ and $R_8$ is selected from branched alkyl, cycloalkyl or aryl groups with 3-10 carbon atoms optionally containing heteroatoms and $R_9$ is a $C_1$-$C_{10}$ alkyl group such as methyl may be used. Examples of such silicon compounds are methylcyclohexyldimethoxysilane (C donor), diphenyldimethoxysilane, methyl-t-butyldimethoxysilane, dicyclopentyldimethoxysilane (D donor), diisopropyldimethoxysilane, (2-ethylpiperidinyl)t-butyldimethoxysilane, (2-ethylpiperidinyl)thexyldimethoxysilane, (3,3,3-trifluoro-n-propyl)(2-ethylpiperidinyl)dimethoxysilane, methyl(3,3,3-trifluoro-n-propyl)dimethoxysilane, N,N-diethylaminotriethoxysilane. Moreover, silicon compounds in which a is 0, c is 3, $R_8$ is a branched alkyl or cycloalkyl group, optionally containing heteroatoms, and $R_9$ is methyl may be used. Examples of such silicon compounds are cyclohexyltrimethoxysilane, t-butyltrimethoxysilane and thexyltrimethoxysilane.

The electron donor compound (iii) is used in such an amount to give a molar ratio between the organoaluminum compound and said electron donor compound (iii) of from 0.1 to 500, including from 1 to 300 and from 3 to 100.

Therefore, it is also described a process for the (co) polymerization of olefins $CH_2$=CHR, in which R is hydrogen or a hydrocarbyl radical with 1-12 carbon atoms, carried out in the presence of a catalyst comprising the product of the reaction between:
  (i) the solid catalyst component of the disclosed technology;
  (ii) an alkylaluminum compound and,
  (iii) optionally an electron-donor compound (external donor).

The polymerization process can be carried out, for example, using slurry polymerization using as diluent an inert hydrocarbon solvent, or bulk polymerization using the liquid monomer (for example propylene) as a reaction medium. Moreover, it is possible to carry out the polymerization process in gas-phase operating in one or more fluidized or mechanically agitated bed reactors.

The polymerization may be carried out at temperature of from 20 to 120° C., including from 40 to 80° C. When the polymerization is carried out in gas-phase the operating pressure is may be between 0.5 and 5 MPa, including between 1 and 4 MPa. In the bulk polymerization the operating pressure may be between 1 and 8 MPa, including between 1.5 and 5 MPa.

The following examples are given in order to illustrate the technology without limiting it.

EXAMPLES

Characterizations
  Determination of X.I.
  2.5 g of polymer and 250 ml of o-xylene were placed in a round-bottomed flask provided with a cooler and a reflux condenser and kept under nitrogen. The obtained mixture was heated to 135° C. and was kept under stirring for about 60 minutes. The final solution was allowed to cool to 25° C. under continuous stirring, and the insoluble polymer was then filtered. The filtrate was then evaporated in a nitrogen flow at 140° C. to reach a constant weight. The content of said xylene-soluble fraction is expressed as a percentage of the original 2.5 grams and then, by difference, the X.I. %.
  Melt Flow Rate (MFR)
  The melt flow rate MIL of the polymer was determined according to ISO 1133 (230° C., 2.16 Kg)

Example 1

Synthesis of 6,6'-dimethyl-[1,1'-biphenyl]-2,2'-diyl dibenzoate

First step

Synthesis of 2-tert-butyl-4-tert-amyl-5-methylphenol

A 100 mL reaction vessel was charged with 2-tert-butyl-5-methylphenol (20 g, 122 mmol), concentrated sulphuric acid (0.12 g, 0.01 eq) and 2-methyl-2-butene (11.5 g, 1.35 eq). The mixture was allowed to stir at ambient temperature for 20 h. The reaction was diluted with ethyl acetate, washed with a saturated aqueous $NaHCO_3$ solution and with a saturated aqueous NaCl solution. The organic phase was dried over $MgSO_4$, filtered and concentrated on a rotary evaporator which resulted in the crude product as yellow oil. Fractional vacuum distillation gave the product that slowly solidified on standing. Yield: 10 g (35%). GC/MS: m/z=234. The white solid was used without further purification.

Second step

Synthesis of 3,3'-di-tert-butyl-5,5'-di-tert-amyl-6,6'-di-methyl1,1'-biphenyl-2,2'-diol A 100 mL reaction vessel was charged with 2-tert-butyl-4-tert-amyl-5-methylphenol (10 g, 42.7 mmol), CuCl(OH)·TMEDA (1.98 g, 0.1 eq) and $CH_2Cl_2$ (10 mL). The mixture was allowed to stir at ambient temperature for 72 h. The suspension was filtered. The mother liquor was dried over $MgSO_4$, filtered and concentrated on a rotary evaporator. The crude oil obtained was stirred with ethanol (30 mL) at ambient temperature for 30 minutes, filtered, washed 3 times with ethanol (30 mL in total) and dry under high vacuum. Yield: 5.6 g (56%). GC/MS: m/z=466. The white solid was used without further purification.

Third step

Synthesis of 6,6'-di-methyl1,1'-biphenyl-2,2'-diol

A 100 mL reaction vessel was charged with 3,3'-di-tert-butyl-5,5'-di-tert-amyl-6,6'-di-methyl1,1'-biphenyl-2,2'-diol (2.0 g, 12.02 mmol), nitromethane (10 mL) and toluene (23 mL). Then $AlCl_3$ (0.74 g, 1.3 eq) was slowly added. The mixture was allowed to stir at ambient temperature for 1 h. The reaction was slowly quenched with a saturated aqueous $NH_4Cl$ solution. The organic phase was washed with a saturated aqueous NaCl solution, then dried over $MgSO_4$, filtered and concentrated on a rotary evaporator which resulted in the crude product as hell yellow solid that was used without further purification.

Fourth step

Synthesis of 6,6'-dimethyl-[1,1'-biphenyl]-2,2'-diyl dibenzoate

A 100 mL reaction vessel was charged with 6,6'-di-methyl1,1'-biphenyl-2,2'-diol, toluene (20 mL) and pyridine (7.8 g, 20 eq). Then benzoyl chloride (1.68 g, 2.8 eq) was slowly added. The mixture was allowed to stir at ambient temperature for 24 h. The reaction was quenched with a saturated aqueous $NH_4Cl$ solution. The organic phase was washed with a saturated aqueous NaCl solution, then dried over $MgSO_4$, filtered and concentrated on a rotary evaporator which resulted in the crude product as hell yellow oil that slowly solidified on standing. The crude solid was stirred with ethanol (10 mL) at ambient temperature for 30 minutes, filtered, washed 3 times with ethanol (10 mL in total) and dry under high vacuum. Yield: 1.4 g (77%). GC/MS: m/z=422.

Example 2

Synthesis of 5,5',6,6'-tetramethyl-[1,1'-biphenyl]-2,2'-diyl dibenzoate

First step

Synthesis of 5,5',6,6'-tetra-methyl-1,1'-biphenyl-2,2'-diol 5,5',6,6'-tetra-methyl-1,1'-biphenyl-2,2'-diol was synthesized in analogy to third step Ex 1, except that 3,3'-di-tertbutyl-5,5',6,6'-tetra-methyl1,1'-biphenyl-2,2'-diol was used instead of 3,3'-di-tert-butyl-5,5'-di-tert-amyl-6,6'-dimethyl1,1'-biphenyl-2,2'-diol.

Second step

Synthesis of 5,5',6,6'-tetramethyl-[1,1'-biphenyl]-2,2'-diyl dibenzoate

A 100 mL reaction vessel was charged with 5,5',6,6'-tetramethyl-1,1'-biphenyl-2,2'-diol (6.8 g, 28.18 mmol) and pyridine (200 mL). Then benzoyl chloride (9.5 g, 2.4 eq) was slowly added. The mixture was allowed to stir at ambient temperature for 20 h. The reaction was quenched with a saturated aqueous $NH_4Cl$ solution. The organic phase was washed with a saturated aqueous NaCl solution, then dried over $MgSO_4$, filtered and concentrated on a rotary evaporator which resulted in the crude product as hell yellow oil that slowly solidified on standing. The crude solid was stirred with ethanol (30 mL) at ambient temperature for 30 minutes, filtered, washed 3 times with ethanol (30 mL in total) and dry under high vacuum. Yield: 5.4 g (42%)—off white powder. GC/MS: m/z=450.

1H-NMR ($CDCl_3$, 298 K): chemical shift (ppm)=7.78 (d, J=7.4 Hz, 4H), 7.48 (t, J=7.4 Hz, 2H), 7.32 (t, J=7.8 Hz, 4H), 7.11 (d, J=8.2 Hz, 2H), 7.05 (d, J=8.2 Hz, 2H), 2.23 (s, 6H) and 1.96 (s, 6H).

Example 3

Synthesis of 5,5',6,6'-tetramethyl-[1,1'-biphenyl]-2,2'-diyl bis(2-methylbenzoate)

6 g of 5,5',6,6'-tetramethyl-[1,1'-biphenyl]-2,2'-diol (24.8 mmol) are charged in a round bottom flask with 120 mL of THF under nitrogen. The mixture is cooled to 0° C. then 1.3 g of NaH (53.6 mmol) are added carefully under stirring, then 6.6 mL of 2-methylbenzoyl chloride (50 mmol) are added dropwise. Cooling bath is removed and the mixture is left to stir at room temperature until GC shows that the reaction is completed (2 hours) Then the mixture is diluted with acidic water (360 mL) and extracted with ethyl acetate (200 mL). The organic layer is washed with water until neutral pH, then is anhydrified over $Na_2SO_4$ and the solvent is distilled off to afford crude product which is crystalized from methanol to afford 11.5 g of white crystalline powder (97% of yield) with a GC purity>99%.

Example 4

Synthesis of 5,5',6,6'-tetramethyl-[1,1'-biphenyl]-2,2'-diyl bis(3,5-dimethylbenzoate)

The procedure is the same as that used for donor at ex 3 except that 3,5-dimethylbenzoyl chloride is used instead of 2-methylbenzoyl chloride.

Example 5

Synthesis of 5,5',6,6'-tetramethyl-[1,1'-biphenyl]-2,2'-diyl bis(2,2-dimethylpropanoate)

The procedure is the same as that used for donor at Example 3 except that trimethylacetyl chloride is used instead of 2-methylbenzoyl chloride.

Example 6

Synthesis of 5,5',6,6'-tetramethyl-[1,1'-biphenyl]-2,2'-diyl bis(diethylcarbamate)

The procedure is the same as that used for donor at Example 3 except that diethylcarbamoyl chloride is used instead of 2-methylbenzoyl chloride. After crystallization from methanol, the pure title compound is obtained with 70% of yield.

Example 7

Synthesis of 6'-((diethylcarbamoyl)oxy)-2',3',5,6-tetramethyl-[1,1'-biphenyl]-2-yl benzoate First step Synthesis of 6'-hydroxy-2',3',5,6-tetramethyl-[1,1'-biphenyl]-2-yl diethylcarbamate In a round bottom flask under nitrogen are added 50 g of 5,5',6,6'-tetramethyl-[1,1'-biphenyl]-2,2'-diol (206 mmol), 400 mL of toluene and 65.3 mL of diethylcarbamoyl chloride (515 mmol) to obtain a yellow solution. Then 22 mL of $TiCl_4$ (206 mmol) are carefully added. A dark red suspension is obtained with evolution of gas. The mixture is heated to 80° C. for one hour then checked via GC which shows a conversion of 95.7%. Diluted HCl is added until mixture turns into pale yellow and organic layer is separated and washed with water until neutral pH, anhydrified over $Na_2SO_4$ and toluene is distilled off to afford crude product which is crystalized from heptane to afford 59 g of powder (84% of yield) with a GC purity>99%.

Second step

Synthesis of 6'-((diethylcarbamoyl)oxy)-2',3',5,6-tetramethyl-[1,1'-biphenyl]-2-yl benzoate 80 mL of THF, 1.2 g of NaH (49 mmol) and 5.4 mL of benzoyl chloride (45 mL) are added in a round bottom flask, under nitrogen at room temperature. Then the mixture is cooled to 0° C. and a solution of 15 g of 6'-hydroxy-2',3',5,6-tetramethyl-[1,1'-biphenyl]-2-yl diethylcarbamate (44 mmol) prepared in the previous step dissolved in 100 mL of THF is added dropwise. Cooling bath is removed and the mixture heated to reflux until GC shows reaction is completed. Then is quenched with diluted HCl and diethyl ether. Organic layer is separated and washed with water until neutral pH, anhydrified over $Na_2SO_4$ and solvent is distilled off to afford crude product which is triturated with 50 mL of pentane to afford 17.3 g of white crystalline powder (90% of yield) with a GC purity>99%.

Example 8

Synthesis of 6'-((ethoxycarbonyl)oxy)-2',3',5,6-tetramethyl-[1,1'-biphenyl]-2-yl benzoate First step Synthesis of 6'-hydroxy-2',3',5,6-tetramethyl-[1,1'-biphenyl]-2-yl benzoate In a round bottom flask under nitrogen are added 30.1 g of 5,5',6,6'-tetramethyl-[1,1'-biphenyl]-2,2'-diol (124 mmol), 100 mL of toluene and 36 mL of benzoyl chloride (310 mmol). Then 13.6 mL of TiCl$_4$ (124 mmol) are carefully added. A dark red suspension is obtained with evolution of gas. The mixture is heated to 80° C. for two hours then checked via GC which shows a complete conversion. Then diluted HCl is added until mixture turns into pale yellow. Ethyl acetate is added and organic layer is separated and washed with water until neutral pH, anhydrified over Na$_2$SO$_4$ and solvent is distilled off to afford crude product which is crystalized from methanol to afford 40 g of the title compound (93% of yield) as white crystalline solid and a GC purity>99%.

Second step

Synthesis of 6'-((ethoxycarbonyl)oxy)-2',3',5,6-tetramethyl-[1,1'-biphenyl]-2-yl benzoate 5.3 g of 6'-hydroxy-2',3',5,6-tetramethyl-[1,1'-biphenyl]-2-yl benzoate (15.3 mmol) are charged in a round bottom flask with 100 mL of THF under nitrogen. Solution is cooled to 0° C. then 1.2 g of NaH (50 mmol) are added carefully under stirring then 5 mL of ethyl chloroformate (52 mmol) are added dropwise. Cooling bath is removed and the mixture is left to stir at room temperature overnight. Then the mixture is diluted with acidic water and extracted with ethyl acetate. The organic layer is washed with water until neutral pH, then is anhydrified over Na$_2$SO$_4$ and the solvent is distilled off to afford crude product which is crystalized from methanol to afford 4.8 of white crystalline powder (75% of yield) with a GC purity>99%.

Example 9

Synthesis of 6'-((cyclohexanecarbonyl)oxy)-2',3',5,6-tetramethyl-[1,1'-biphenyl]-2-yl benzoate This compound was synthesized in analogy to the second step of Example 8, except that cyclohexanecarbonyl chloride was used instead of ethyl chloroformate.

Example 10

Synthesis of 6'-methoxy-2',3',5,6-tetramethyl-[1,1'-biphenyl]-2-yl benzoate

This compound was synthesized in analogy to the second step of Example 8, except that methyl iodide was used instead of ethyl chloroformate. Yield 95%.

Example 11

Synthesis of 3,3'-di-tert-butyl-5,5',6,6'-tetramethyl-[1,1'-biphenyl]-2,2'-diyl dibenzoate A 250 mL reaction vessel was charged with 3,3'-di-tert-butyl-5,5',6,6'-tetra-methyl1,1'-biphenyl-2,2'-diol (10.0 g, 28.21 mmol), 4-dimethylamino-pyridine (6 g, 2.3 eq) and pyridine (100 mL). Then benzoyl chloride (9.5 g, 2.4 eq) was slowly added. The mixture was allowed to reflux for 30 h. The reaction was quenched with a saturated aqueous NH$_4$Cl solution. The organic phase was washed with a saturated aqueous NaCl solution, then dried over MgSO$_4$, filtered and concentrated on a rotary evaporator which resulted in the crude product as hell yellow oil that slowly solidified on standing. The crude solid was stirred with ethanol (20 mL) at ambient temperature for 30 minutes, filtered, washed 2 times with ethanol (20 mL in total) and dry under high vacuum. Yield: 10.5 g (66%)—off white powder. GC/MS: m/z=562.

1H-NMR (CDCl$_3$, 298 K): chemical shift (ppm)=7.85 (bd, J=8 Hz, 4H), 7.48 (bt, J=8 Hz, 2H), 7.34 (t, J=8 Hz, 4H), 6.92 (s, 2H), 2.17 (s, 6H), 1.95 (s, 6H) and 1.15 (s, 18H).

Example 12

Synthesis of 3,3'-di-tert-butyl-5,5',6,6'-tetramethyl-[1,1'-biphenyl]-2,2'-diyl bis(4-propylbenzoate)

This compound was synthesized in analogy to Example 11, except that 4-n-propyl-benzoyl chloride was used instead of benzoyl chloride. Yield: 5.8 g (33%)—off white powder. GC/MS: m/z=646.

Example 13

Synthesis of 3,3'-di-tert-butyl-5,5',6,6'-tetramethyl-[1,1'-biphenyl]-2,2'-diyl diacetate A 250 mL reaction vessel was charged with 3,3'-di-tert-butyl-5,5',6,6'-tetra-methyl1,1'-biphenyl-2,2'-diol (10.0 g, 28.21 mmol) and THF (100 mL). Then NaH (2.6 g, 2,4 eq, 60% in oil) was slowly added. The mixture was allowed to stir at ambient temperature for 2 h. Then acetyl chloride (5.6 g, 2.5 eq) was slowly added. The mixture was allowed to stir at ambient temperature for 21 h. The reaction was quenched with a saturated aqueous NH$_4$Cl solution. The organic phase was washed with a saturated aqueous NaCl solution, then dried over MgSO$_4$, filtered and concentrated on a rotary evaporator which resulted in the crude product as yellow-orange paste. This crude paste was stirred with ethanol (20 mL) at ambient temperature for 30 minutes, filtered, washed 3 times with ethanol (20 mL in total) and dry under high vacuum. Yield: 3.5 g (29%)—yellow powder. GC/MS: m/z=438.

Example 14

Synthesis of 3,3'-di-tert-butyl-5,5',6,6'-tetramethyl-[1,1'-biphenyl]-2,2'-diyl di pentanoate This compound was synthesized in analogy to Example 13, except that valeryl chloride (3 eq) was used instead of acetyl chloride and that 3 equivalent of sodium hydride was used instead of 2.4. Yield: 4.7 g (32%)—off white powder. GC/MS: m/z=522.

Example 15

Synthesis of 2'-acetoxy-3,3'-di-tert-butyl-5,5',6,6'-tetramethyl-[1,1'-biphenyl]-2-yl benzoate First step Synthesis of 6'-hydroxy-2',3',5,6-tetramethyl-5',3-ditert-butyl-[1,1'-biphenyl]-2-yl benzoate A 100 mL reaction vessel was charged with 3,3'-di-tert-butyl-5,5',6,6'-tetra-methyl1,1'-biphenyl-2,2'-diol (5.5 g, 15.5 mmol), 4-dimethylamino-pyridine (0.95 g, 0.5 eq) and pyridine (50 mL). Then benzoyl chloride (2.5 g, 1.15 eq) was slowly added. The mixture was allowed to reflux for 10 h. The reaction was quenched with a saturated aqueous NH$_4$Cl solution. The organic phase was washed with a saturated aqueous NaCl solution, then dried over MgSO$_4$, filtered and concentrated on a rotary evaporator which resulted in the crude product as hell yellow solid. The crude solid was stirred with ethanol (10 mL) at ambient temperature for 30 minutes, filtered, washed 2 times with ethanol (15 mL in total) and dry under high vacuum. Yield: 6.8 g (96%)—off white powder. GC/MS: m/z=458.

Second step

Synthesis of 2'-acetoxy-3,3'-di-tert-butyl-5,5',6,6'-tetramethyl-[1,1'-biphenyl]-2-yl benzoate A 100 mL reaction vessel was charged with the former described intermediate (6.8 g, 14.8 mmol) and THF (60 mL). Then NaH (0.88 g, 1.5 eq, 60% in oil) was slowly added. The mixture was allowed to stir at ambient temperature for 2 h. Then acetyl chloride (1.8 g, 1.5 eq) was slowly added. The mixture was allowed to stir at ambient temperature for 72 h then quenched with a saturated aqueous NH$_4$Cl solution. The organic phase was washed with a saturated aqueous NaCl solution, dried over MgSO$_4$, filtered and concentrated on a rotary evaporator which resulted in the crude product as yellow solid. This crude solid was stirred with pentane (20 mL) at ambient temperature for 30 minutes, filtered, washed 4 times with pentane (40 mL in total) and dry under high vacuum. Yield: 4.7 g (64%)—beige powder. GC/MS: m/z=500.

Example 16

Synthesis of 2'-((diethylcarbamoyl)oxy)-[1,1'-biphenyl]-2-yl benzoate

First step

Synthesis of 6'-hydroxy-[1,1'-biphenyl]-2-yl benzoate

In a round bottom flask under nitrogen are added 15 g of 2,2'-biphenol (80.8 mmol), 60 mL of toluene and 23.5 mL of benzoyl chloride (202 mmol). Then 8.9 mL of TiCl$_4$ (80.8 mmol) are carefully added. A dark red suspension is obtained with evolution of gas. The mixture is heated to 80° C. for two hours then checked via GC which shows a complete conversion. Then diluted HCl is added until mixture turns into pale yellow. Diethyl ether is added and organic layer is separated and washed with water until neutral pH, anhydrified over Na$_2$SO$_4$ and solvent is distilled off to afford crude product which is crystalized from methanol resulting in 23 g of the title compound as white crystalline solid (yield 98%) and a GC purity>99%.

Second step

Synthesis of 2'-((diethylcarbamoyl)oxy)[1,1'-biphenyl]-2-yl benzoate

A 500 mL reaction vessel was charged with the former described intermediate (11.5 g, 39.6 mmol), diethylcarbamoyl chloride (5.9 g, 1.1 eq), and CH$_2$Cl$_2$ (225 mL). Then AlCl$_3$ (5.95 g, 1.13 eq) was slowly added. The mixture was allowed to stir at ambient temperature for 24 h, then quenched with a saturated aqueous NH$_4$Cl solution. The organic phase was washed with a saturated aqueous NaCl solution, dried over MgSO$_4$, filtered and concentrated on a rotary evaporator which resulted in the crude product as yellow oil. This crude oil was crystallized in ethanol (20 mL), washed 2 times with ethanol (20 mL in total) and dry under high vacuum. Yield: 12.8 g (81%)—beige powder. GC/MS: m/z=389.

Example 17

Synthesis of [1,1'-binaphthalene]-2,2'-diyl dibenzoate

This compound was synthesized in analogy to second step Example 2, except that 1,1'-bi-2-naphthol was used instead of 5,5',6,6'-tetra-methyl-1,1'-biphenyl-2,2'-diol. Yield: 10.8 g (78%)—off white powder. GC/MS: m/z=494.
1H-NMR (CDCl$_3$, 298 K): chemical shift (ppm)=7.97 (d, J=12 Hz, 2H), 7.89 (d, J=8 Hz, 2H), 7.62 (dd, J=5.6 Hz and J=1.2 Hz, 4H), 7.55 (d, J=8.9 Hz, 2H), 7.45-7.21 (m, 12H).

Example 18

Synthesis of 2'-((diethylcarbamoyl)oxy)-[1,1'-binaphthalen]-2-yl benzoate

This compound was synthesized in analogy to Example 16, except that 1,1'-bi-2-naphthol was used. Yield: 17.0 g (81%—2 steps)—off white powder. GC/MS: m/z=489.

Example 19

Synthesis of 5,5',6,6',7,7',8,8'-octahydro-[1,1'-binaphthalene]-2,2'-diyl dibenzoate This compound was synthesized in analogy to second step Example 2, except that 5,5',6,6',7,7',8,8'-Octahydro-1,1'-bi-2-naphthol was used instead of 5,5',6,6'-tetra-methyl-1,1'-biphenyl-2,2'-diol. Yield: 7.1 g (83%)—off white powder. GC/MS: m/z=502.

Example 20

Synthesis of 2,2',3,3'-tetrahydro-1H,1'H-[4,4'-biindene]-5,5'-diyl dibenzoate

First step

Synthesis of 6-tert-butyl-5-indanol

A 100 mL reaction vessel was charged with 5-indanol (25 g, 185 mmol), tert-butyl chloride (52 g, 3 eq) and concentrated sulphuric acid (0.27 g, 0.015 eq). The mixture was allowed to stir at 55° C. for 20 h, then was diluted with ethyl acetate, washed with a saturated aqueous NaHCO$_3$ solution and with a saturated aqueous NaCl solution. The organic phase was dried over MgSO$_4$, filtered and concentrated on a rotary evaporator which resulted in the crude product as brown liquid that slowly solidified on standing. The crude solid obtained was stirred with pentane (20 mL) at ambient temperature for 30 minutes, filtered, washed 2 times with pentane (20 mL in total) and dry under high vacuum. Yield: 24.8 g (71%). GC/MS: m/z=190. The white solid was used without further purification.

Second step

Synthesis of 6,6'-di-tert-butyl-2,2',3,3'-tetrahydro-1H,1'H-[4,4'-biindene]-5,5'-diol 6,6'-di-tert-butyl-2,2',3,3'-tetrahydro-1H,1'H-[4,4'-biindene]-5,5'-diol was synthesized in analogy to second step Example 1 expect that 6-tert-butyl-5-indanol, prepared in the previous step, was used instead of 2-tert-butyl-4-tert-amyl-5-methylphenol. The crude solid obtained was stirred with pentane (30 mL) at ambient temperature for 30 minutes, filtered, washed 3 times with pentane (40 mL in total) and dry under high vacuum. Yield: 13.3 g (54%). GC/MS: m/z=378. The beige solid was used without further purification.

Third step

Synthesis of 2,2',3,3'-tetrahydro-1H,1'H-[4,4'-biindene]-5,5'-diol 2,2',3,3'-tetrahydro-1H,1'H-[4,4'-biindene]-5,5'-diol was synthesized in analogy to third step Example 1.

Fourth step

Synthesis of 2,2',3,3'-tetrahydro-1H,1'H-[4,4'-biindene]-5,5'-diyl dibenzoate

The last step was done in analogy to second step Example 2. Yield: 6.4 g (79%)—beige powder. GC/MS: m/z=474.

Example 21

Synthesis of 6,6'-di-tert-butyl-2,2',3,3'-tetrahydro-1H,1'H-[4,4'-biindene]-5,5'-diyl dibenzoate This compound was synthesized in analogy to second step Example 11. Yield: 5.4 g (51%). GC/MS: m/z=586.

Example 22

Synthesis of 6'-(benzoyloxy)-2',3',5,6-tetramethyl-[1,1'-biphenyl]-2-yl piperidine-1-carboxylate 5 g of 6'-hydroxy-2',3',5,6-tetramethyl-[1,1'-biphenyl]-2-yl benzoate (14.5 mmol), prepared in the first step of example 8, are added in a round bottom flask with 25 mL pyridine and 5 g of 1-piperidinecarbonyl chloride (34 mmol). The mixture is heated to 100° C. and kept at this temperature until GC shows complete conversion (13 hours). Then is quenched with 100 mL of diluted HCl and diethyl ether. The organic layer is separated and washed with water until neutral pH. anhydrified over Na2SO4 and solvent is distilled off to afford 9 g crude product which is purified by means of chromatography (SiO2)—cyclohexane/ethyl acetate: 9:1. Yield: 3.8 g (58%)—viscous oil.

Example 25

Synthesis of 6'-hydroxy-2',3',5,6-tetramethyl-[1,1'-biphenyl]-2-yl diethylcarbamate Synthesis of 6'-hydroxy-2',3',5,6-tetramethyl-[1,1'-biphenyl]-2-yl diethylcarbamate has been described in the first step of Example 7.

Example 26

Synthesis of 2'-hydroxy-[1,1'-biphenyl]-2-yl diethylcarbamate

In a round bottom flask under nitrogen are added 50 g of 2,2'-biphenol (269 mmol), 200 mL of toluene and 85 mL of diethylcarbamoyl chloride (672 mmol). Then 29 mL of TiCl4 (269 mmol) are carefully added. A dark red suspension is obtained with evolution of gas. The mixture is heated to 80° C. for two hours then checked via GC which shows a complete conversion. DMSO is added until the precipitate is completely dissolved and conc. HCl is added until mixture turns into pale yellow. Diethyl ether is added and organic layer is separated and washed with water until neutral pH, anhydrified over Na2SO4 and solvent is distilled off to afford crude product which is crystalized from methanol to afford the title compound as white crystalline solid and a GC purity>99%.

Example 27

Synthesis of 2'-hydroxy-[1,1'-binaphthalen]-2-yl benzoate

This compound was synthesized in analogy to first step Example 16, except that 1,1'-bi-2-naphthol was used instead of 1,1'-biphenyl-2,2'-diol. Yield: 29.5 g (87%)—off white powder. GC/MS: m/z=390.

1H-NMR (CDCl3, 298 K): =8.11 (d, J=8.9 Hz, 1H), 7.99 (d, J=8.2 Hz, 1H), 7.79-7.75 (m, 2H), 7.65 (dd, J=8.2 Hz and J=1.2 Hz, 2H), 7.55-7.13 (m, 11H).

Example 28

Synthesis of 6'-hydroxy-2',3',5,6-tetramethyl-[1,1'-biphenyl]-2-yl benzoate

Synthesis of 6'-hydroxy-2',3',5,6-tetramethyl-[1,1'-biphenyl]-2-yl benzoate is described in the first step of Example 8.

Comp. Example 1

Synthesis of [1,1'-biphenyl]-2,2'-diyl di-4-n-propylbenzoate

This compound was synthesized in analogy to second step Example 2, except that 1,1'-biphenyl-2,2'-diol was used instead of 5,5',6,6'-tetra-methyl-1,1'-biphenyl-2,2'-diol. The crude oil was purified by means of chromatography (SiO2)—Cyclohexane/CH2Cl2:6/4. Yield: 7.2 g (28%)—viscous colourless oil. GC/MS: m/z=478.

General Procedure for Preparation of the Spherical Adducts

An initial amount of microspheroidal MgCl2·2.8C2H5OH was prepared according to the method described in Example 2 of WO98/44009, but operating on larger scale.

Procedure for the Preparation of the Solid Catalyst Component Using Donors Example 1-21 and Comp. Example 1.

Into a 500 mL round bottom flask, equipped with mechanical stirrer, cooler and thermometer 250 mL of TiCl4 were introduced at room temperature under nitrogen atmosphere. After cooling to 0° C., while stirring, the internal donor and 10.0 g of the spherical adduct (prepared as described above) were sequentially added into the flask. The amount of charged internal donor was such to charge a Mg/donor molar ratio of 6. The temperature was raised to 100° C. and maintained for 2 hours. Thereafter, stirring was stopped, the solid product was allowed to settle and the supernatant liquid was siphoned off at 100° C. After the supernatant was removed, additional fresh TiCl4 was added to reach the initial liquid volume again. The mixture was then heated at 120° C. and kept at this temperature for 1 hour. Stirring was stopped again, the solid was allowed to settle and the supernatant liquid was siphoned off.

The solid was washed with anhydrous hexane six times (6×100 mL) in temperature gradient down to 60° C. and one time (100 mL) at room temperature. The obtained solid was then dried under vacuum and analyzed.

Procedure for the Preparation of the Solid Catalyst Component Using Donors Example 23-24.

The solid catalyst component was prepared according to the same procedure of Examples 1-21 with the difference that the first treatment with TiCl4 was carried out at 120° C. instead of 100° C.

Procedure for the Preparation of the Solid Catalyst Component Using Donors Example 25-28.

Into a 500 mL round bottom flask, equipped with mechanical stirrer, cooler and thermometer 250 mL of $TiCl_4$ were introduced at room temperature under nitrogen atmosphere. After cooling to 0° C., while stirring, ethyl benzoate and 10.0 g of the spherical adduct (prepared as described above) were sequentially added into the flask. The amount of charged ethyl benzoate was such to charge a Mg/EB molar ratio of 4. The temperature was raised to 100° C. and maintained for 2 hours. Thereafter, stirring was stopped, the solid product was allowed to settle and the supernatant liquid was siphoned off at 100° C. After the supernatant was removed, additional fresh $TiCl_4$ was added to reach the initial liquid volume again followed by the addition of the internal donor with Mg/donor ratio of 6. The mixture was then heated at 120° C. and kept at this temperature for 1 hour. Stirring was stopped again, the solid was allowed to settle and the supernatant liquid was siphoned off. This last hot treatment at 120° C. for 1 hour is repeated an additional time. Stirring was stopped again, the solid was allowed to settle and the supernatant liquid was siphoned off.

The solid was washed with anhydrous hexane six times (6×100 mL) in temperature gradient down to 60° C. and one time (100 mL) at room temperature. The obtained solid was then dried under vacuum and analyzed.

General Procedure for the Polymerization of Propylene

A 4-litre steel autoclave equipped with a stirrer, pressure gauge, thermometer, catalyst feeding system, monomer feeding lines and thermostating jacket, was purged with nitrogen flow at 70° C. for one hour. Then, at 30° C. under propylene flow, were charged in sequence with 75 mL of anhydrous hexane, 0.76 g of $AlEt_3$, the external electron donor indicated in Table 1 (if used) and 0.006÷0.010 g of solid catalyst component. The autoclave was closed; subsequently 2.0 NL of hydrogen were added. Then, under stirring, 1.2 kg of liquid propylene was fed. The temperature was raised to 70° C. in five minutes and the polymerization was carried out at this temperature for two hours. At the end of the polymerization, the non-reacted propylene was removed; the polymer was recovered and dried at 70° C. under vacuum for three hours. Then the polymer was weighed and fractionated with o-xylene to determine the amount of the xylene insoluble (X.I.) fraction.

Examples 1-28 and comp. Example 1

The catalyst components were prepared according to the procedures described above using the donors prepared in Example 1-28 and comp. Example 1 and were tested in polymerization of propylene, using the polymerization procedure described above. The results are listed in Table 1.

TABLE 1

Composition and performance of exemplified catalysts

| | | | Polymerization | | |
|---|---|---|---|---|---|
| Ex. | Internal Donor Name | ED | Mileage kg/g | XI % wt | MIL g/10' |
| 1 | 6,6'-dimethyl-[1,1'-biphenyl]-2,2'-diyl dibenzoate | D | 42 | 97.3 | 3.5 |
| 2 | 5,5',6,6'-tetramethyl-[1,1'-biphenyl]-2,2'-diyl dibenzoate | D | 56 | 97.2 | 3.6 |
| 3 | 5,5',6,6'-tetramethyl-[1,1'-biphenyl]-2,2'-diyl bis(2-methylbenzoate) | D | 57 | 97.7 | 1.4 |
| 4 | 5,5',6,6'-tetramethyl-[1,1'-biphenyl]-2,2'-diyl bis(3,5-dimethylbenzoate) | D | 47 | 96.9 | 6.5 |
| 5 | 5,5',6,6'-tetramethyl-[1,1'-biphenyl]-2,2'-diyl bis(2,2-dimethylpropanoate) | D | 47 | 96.8 | 1.2 |
| 6 | 5,5',6,6'-tetramethyl-[1,1'-biphenyl]-2,2'-diyl bis(diethylcarbamate) | D | 48 | 96.6 | 8.3 |
| 7 | 6'-((diethylcarbamoyl)oxy)-2',3',5,6-tetramethyl-[1,1'-biphenyl]-2-yl benzoate | D<br>C | 63<br>70 | 97.7<br>97.4 | 0.6<br>1.0 |
| 8 | 6'-((ethoxycarbonyl)oxy)-2',3',5,6-tetramethyl-[1,1'-biphenyl]-2-yl benzoate | D | 57 | 97.2 | 6.5 |
| 9 | 6'-((cyclohexanecarbonyl)oxy)-2',3',5,6-tetramethyl-[1,1'-biphenyl]-2-yl benzoate | D | 48 | 97.4 | 1.8 |
| 10 | 6'-methoxy-2',3',5,6-tetramethyl-[1,1'-biphenyl]-2-yl benzoate | D | 86 | 96.5 | 2.0 |
| 11 | 3,3'-di-tert-butyl-5,5',6,6'-tetramethyl-[1,1' biphenyl]-2,2'-diyl dibenzoate | D | 55 | 97.1 | 3.4 |
| 12 | 3,3'-di-tert-butyl-5,5',6,6'-tetramethyl-[1,1' biphenyl]-2,2'-diyl bis(4-propylbenzoate) | D | 65 | 96.9 | 2.7 |
| 13 | 3,3'-di-tert-butyl-5,5',6,6'-tetramethyl-[1,1' biphenyl]-2,2'-diyl diacetate | D | 57 | 97.3 | 3.3 |
| 14 | 3,3'-di-tert-butyl-5,5',6,6'-tetramethyl-[1,1' biphenyl]-2,2'-diyl dipentanoate | D | 55 | 97.1 | 2.7 |
| 15 | 2'-acetoxy-3,3'-di-tert-butyl-5,5',6,6'-tetramethyl-[1,1'-biphenyl]-2-yl benzoate | D | 65 | 97.5 | 2.4 |
| 16 | 2'-((diethylcarbamoyl)oxy)-[1,1'-biphenyl]-2-yl benzoate | D | 45 | 96.5 | 3.8 |
| 17 | [1,1'-binaphthalene]-2,2'-diyl dibenzoate | D | 67 | 96.7 | 3.0 |

TABLE 1-continued

Composition and performance of exemplified catalysts

| Ex. | Internal Donor Name | ED | Polymerization Mileage kg/g | XI % wt | MIL g/10' |
|---|---|---|---|---|---|
| 18 | 2'-((diethylcarbamoyl)oxy)-[1,1'-binaphthalen]-2-yl benzoate | D | 50 | 97.8 | 1.0 |
| 19 | 5,5',6,6',7,7',8,8'-octahydro-[1,1'-binaphthalene]-2,2'-diyl dibenzoate | D | 53 | 96.9 | 2.3 |
| 20 | 2,2',3,3'-tetrahydro-1H,1'H-[4,4'-biindene]-5,5'-diyl dibenzoate | D | 46 | 96.9 | 2.1 |
| 21 | 6,6'-di-tert-butyl-2,2',3,3'-tetrahydro-1H,1'H-[4,4'-biindene]-5,5'-diyl dibenzoate | D | 58 | 96.7 | 4.6 |
| 22 | 6'-(benzoyloxy)-2',3',5,6-tetramethyl-[1,1'-biphenyl]-2-yl piperidine-1-carboxylate | D | 56 | 97.5 | 0.7 |
| 23 | 6'-methoxy-2',3',5,6-tetramethyl-[1,1'-biphenyl]-2-yl benzoate | D | 77 | 97.2 | 2.7 |
| 24 | 3,3'-di-tert-butyl-5,5',6,6'-tetramethyl-[1,1'-biphenyl]-2,2'-diyl dibenzoate | D | 65 | 97.0 | 2.3 |
| 25 | 6'-hydroxy-2',3',5,6-tetramethyl-[1,1'-biphenyl]-2-yl diethylcarbamate | D | 75 | 97.7 | 0.9 |
| 26 | 2'-hydroxy-[1,1'-biphenyl]-2-yl diethylcarbamate | D | 55 | 96.2 | 4.3 |
| 27 | 2'-hydroxy-[1,1'-binaphthalen]-2-yl benzoate | D | 82 | 97.0 | 2.1 |
| 28 | 6'-hydroxy-2',3',5,6-tetramethyl-[1,1'-biphenyl]-2-yl benzoate | D | 78 | 97.0 | 2.9 |
| Comp. Ex. 1 | [1,1'-biphenyl]-2,2'-diyl bis(4-propylbenzoate) | D | 49 | 94.1 | 10.8 |

ED: External Donor.
C: methylcyclohexyldimethoxysilane
D: dicyclopentyldimethoxysilane

What is claimed is:

1. A solid catalyst component for the polymerization of olefins comprising Mg, Ti, Cl and at least an electron donor compound wherein the solid catalyst component is the reaction product obtained by bringing into contact a Mg compound and a Ti compound having at least a Ti-halogen bond with an electron donor selected from derivatives of formula (I):

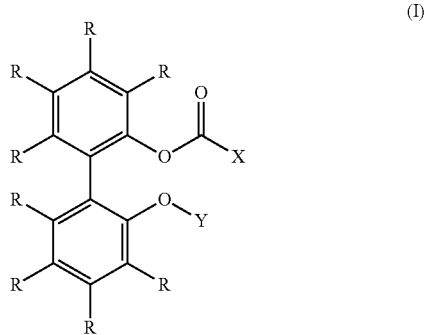

where X is selected from $R^1$, —OR and —$NR_2$, Y is selected from hydrogen, $R^1$, —$COR^1$, —$CONR_2$, and —$MZ_{(n-1)}$; the R groups, equal to or different from each other, are selected from hydrogen, halogen and $C_1$-$C_{15}$ hydrocarbon groups, optionally containing an heteroatom selected from halogen, P, S, N, O and Si, which can be fused together to form one or more cycles and at least one of the R groups is different from hydrogen and selected from halogen or $C_1$-$C_{15}$ hydrocarbon groups; M is an element belonging to Groups 2 or 4-13 of the Periodic Table of Elements; n is the valence of M; Z is halogen or $OR^1$ and the $R^1$ group is a $C_1$-$C_{15}$ aliphatic or aromatic hydrocarbon group; with the proviso that when X is a substituted or unsubstituted phenyl group, and Y is a substituted or unsubstituted benzoyl group, at least one of the R groups on the phenyl rings of the structure of formula (I) is not hydrogen.

2. The catalyst component of claim 1, in which at least two of the R groups are different from hydrogen.

3. The catalyst component of claim 2, in which at least 3 of the R groups are different from hydrogen.

4. The catalyst component of claim 1, in which the two phenyl rings of formula (I) have the same substitution pattern.

5. The catalyst component of claim 4, in which the R groups are selected from $C_1$-$C_{10}$ alkyl groups.

6. The catalyst component of claim 1, in which the $R^1$ groups are selected from $C_1$-$C_{10}$ alkyl groups, $C_6$-$C_{15}$ aryl groups and alkylaryl groups.

7. The catalyst component of claim 1, in which R radicals in the —$NR_2$ and —$CONR_2$ groups are selected from $C_1$-$C_{10}$ alkyl groups.

8. The catalyst component of claim 1, in which X is $R^1$ and Y is selected from hydrogen, $R^1$, —$COR^1$, and —$CONR_2$.

9. The catalyst component of claim 1, in which Y is selected from —$COR^1$ and —$CONR_2$.

10. The solid catalyst component of claim 8, in which X is a $C_6$-$C_{15}$ aryl or alkylaryl group and Y is methyl.

11. The solid catalyst component of claim 1, in which X is —$NR_2$ and Y is selected from hydrogen and —$COR^1$.

12. The solid catalyst component of claim 11, in which $R^1$ is a $C_6$-$C_{15}$ aryl or alkylaryl group and R is a linear $C_1$-$C_5$ alkyl group.

13. A catalyst for the polymerization of olefins comprising the product of the reaction between:
 (i) the solid catalyst component according to claim 1 and
 (ii) an alkylaluminum compound and optionally,
 (iii) an external electron donor compound.

14. A process for the (co)polymerization of olefins of the formula $CH_2=CHR$, in which R is hydrogen or a hydrocarbyl radical with 1-12 carbon atoms, carried out in the presence of a catalyst system comprising the product of the reaction between:
  i. the solid catalyst component according to claim 1;
  ii. an alkylaluminum compound; and
  iii. optionally an external donor compound;
    wherein the catalyst system is contacted with olefins of the formula $CH_2=CHR$ under conditions capable of polymerizing the olefins.

* * * * *